United States Patent [19]

Lueders

[11] Patent Number: 4,820,814

[45] Date of Patent: Apr. 11, 1989

[54] PROCESS FOR PRODUCING COLORLESS BUTYLOLIGOGLYCOSIDES

[75] Inventor: Harald Lueders, Recklinghausen, Fed. Rep. of Germany

[73] Assignee: Hüls Aktiengesellschaft, Marl, Fed. Rep. of Germany

[21] Appl. No.: 40,601

[22] Filed: Apr. 21, 1987

[30] Foreign Application Priority Data

Jul. 23, 1986 [DE] Fed. Rep. of Germany ....... 3624863

[51] Int. Cl.$^4$ ..................... C07H 1/06; C07H 15/04; C07H 15/00; C07G 3/00
[52] U.S. Cl. .................... 536/127; 536/4.1; 536/124; 536/18.5; 536/18.6
[58] Field of Search .............. 536/4.1, 18.5, 18.6, 536/124, 127

[56] References Cited

U.S. PATENT DOCUMENTS

| | | | |
|---|---|---|---|
| 2,390,507 | 12/1945 | Cantor | 536/18.6 |
| 3,450,690 | 6/1969 | Gibbons et al. | 536/18.5 |
| 3,547,828 | 12/1970 | Mansfield et al. | 536/4.1 |
| 3,565,885 | 2/1971 | Molotsky et al. | 536/18.6 |
| 3,974,138 | 8/1976 | Lew | 536/18.6 |
| 4,683,297 | 7/1987 | Yanami et al. | 536/18.6 |
| 4,721,780 | 1/1988 | McDaniel, Jr. et al. | 536/18.6 |

FOREIGN PATENT DOCUMENTS 0099183 1/1984 European Pat. Off. .......... 536/18.6

*Primary Examiner*—Ronald W. Griffin
*Assistant Examiner*—Nancy S. Carson
*Attorney, Agent, or Firm*—Oblon, Fisher, Spivak, McClelland & Maier

[57] ABSTRACT

The dark-colored solutions obtained in the preparation of butyloligoglycosides from saccharides and butanol are adjusted to an acidity of 0 to 12 mg of KOH/g. Colorless or light-colored butyloligoglycosides are then extracted from them by water, optionally after the addition of a nonpolar solvent, and are then isolated from the aqueous phase in a conventional way.

13 Claims, No Drawings

PROCESS FOR PRODUCING COLORLESS BUTYLOLIGOGLYCOSIDES

BACKGROUND OF THE INVENTION

1. Field of the Invention

The invention relates to a process for producing colorless or light-colored butylglycosides and/or butyloligoglycosides by treatment with base followed by isolation from an aqueous mixture.

2. Discussion of the Background

Butylglycosides, butyloligoglycosides, and their mixtures are interesting polyols that are available from carbohydrates, a replaceable raw material resource. They are gaining increasing importance as intermediates in the production of polyurethanes and surfactants based on long-chained alkylglycosides.

Butyloligoglycosides are generally prepared by heating saccharides, butanol, and an acid. Substantial amounts of byproducts are formed in this process that impart an unattractive color and an unpleasant odor to the glycosides. These byproducts occur especially when using polysaccharides as starting materials, which have to be reacted under vigorous conditions.

Colorless byproducts are also formed that can lead to discolorations in the further use of the glycosides or in purification operations. This applies particularly to the acid catalyzed transacetalization to form alkyloligoglycosides with long-chained alkyl groups.

Various processes are known for improving the color of the alkyloligoglycosides. Thus, European Patent No. 102 558 describes a process by which the color quality of the glycosides is improved by adding alkali metal borates to the reaction batch. The borates are added in an amount at least equivalent to the catalytic sulfuric acid. Starch cannot be used as a starting material in this process, since the butanolysis of starch is not effectively catalyzed by boric acid.

According to U.S. Pat. No. 4,483,979, dyes can be extracted from alkylpolysaccharides with long-chained alkyl groups using polar solvents under anhydrous conditions. Glycosides with 1 to 2 glycose units are coextracted in this process. Since the butyloligoglucosides of industrial interest with 1 to 3 glucose units are readily soluble in acetone and other polar solvents, these products cannot be selectively freed of colored impurities by this process.

In European Patent No. 99 183, alkylglycosides are prepared from polysaccharides containing water and alcohols. The reaction is carried out in the presence of cosolvents such as methanol, ethanol, ethylene glycol, or acetone. The reaction mixture has a high content of unreacted glucose. The reaction product is improved in color, but requires increased distillation cost for purification because of the cosolvents.

European Patent No. 77 167 describes the use of reducing agents such as hypophosphorous acid in the glucose/butanol/acid reaction mixture. With monosaccharides this process leads to glycosides of improved color, but when using starch under vigorous reaction conditions it leads to dark-colored products.

Dark-colored products are also obtained with starch under vigorous reaction conditions when using hydroxypolycarboxylic acids by the method of U.S. Pat. No. 4,465,828.

European Patent No. 132 046 describes a process for preparing alkylglycosides by which the color quality is improved by neutralizing the reaction batch with an alkali metal alkoxide after the reaction. The optically detectable byproducts are reduced by about half by this process.

Color control of alkylglycosides is described in European Patent No. 165 721. The product is bleached in this case with hydrogen peroxide, and the color is then stabilized with a compound that liberates $SO_2$. However, this process provides products from which dark-colored alkylglycosides are obtained in transacetalization.

SUMMARY OF THE INVENTION

Accordingly, one object of the present invention is to provide a process for producing colorless or light-colored butylglycosides or butyloligoglycosides.

Another object of the invention is to provide a process for producing butylglycosides and butyloligoglycosides that causes no severe discoloration in transacetalizations to form alkyloligoglycosides with long-chain alkyl groups.

These objects and other objects of the present invention which will become apparent from the following specification have been achieved by the present process for producing colorless or light-colored butylglycosides or butyloligoglycosides from a crude butylglycoside or butyloligoglycoside reaction product, comprising the steps of:

(a) adjusting the acid number of the crude reaction product to 0-12 mg KOH/g;

(b) extracting the butylglycosides and butyloligoglycosides from the adjusted product mixture with water; and (c) isolating the butylglycosides and butyloligoglycosides from the water extract.

DETAILED DESCRIPTION OF THE PREFERRED EMBODIMENTS

It is the purpose of this invention to provide a process for producing colorless or light-colored butylglycosides and butyloligoglycosides that cause no severe discolorations in transacetalizations to form alkyloligoglycosides with long-chained alkyl groups.

Surprisingly, the problems noted above are solved by subjecting the butyloligoglycosides and butylglycosides prepared by known methods to a special extraction. The crude product is first adjusted with an acid or a base to an acid number of 0 to 12 mg of KOH/g. The butylglycosides or butyloligoglycosides, after the optional addition of a hydrophobic solvent, are then extracted from the mixture with water, after which they are isolated from the aqueous phase by conventional methods.

The butylglycosides and butyloligoglycosides can be prepared by the methods of German OS No. 19 43 689 or U.S. Pat. No. 3,375,243, for example. The solutions of butyloligoglycosides in butanol that are obtained initially have a very dark color.

Polysaccharides such as starch, oligosaccharides, or monosaccharides can be used in the preparation of the butylglycosides and butyloligoglycosides. Preferred monosaccharides are hexoses such as dextrose, glucose, mannose, or galactose, or pentoses such as ribose, arabinose, xylose, or lyxose.

Fluid mixtures that contain predominantly butylglycosides and butyloligoglycosides, or solutions of the glycosides, can be used as the crude product for the extraction. The reaction products from saccharide and butanol are preferably used.

The acid number of the crude mixtures or solutions is adjusted to a value of 0 to 12 mg of KOH/g by adding an acid or a base. An acid number of 0.01 to 3 mg of KOH/g is preferred. Acid numbers of 0.05 to 1 mg of KOH/g are especially preferred. In the case of alkaline solutions the extraction does not proceed satisfactorily. With acid numbers above 12 mg of KOH/g there is an increased risk of glycoside cleavage during the extraction. To adjust the acid number, sulfuric acid or p-toluenesulfonic acid are preferred as the acid, and a sodium hydroxide solution is preferred as the base. It is preferable to use the acid used in the preparation process.

Up to 2 parts of hydrophobic solvent can be added for 1 part of adjusted mixture or solution. Examples of preferred solvents of this type are aromatic hydrocarbons such as toluene, xylene, or mixtures of them.

The adjusted mixtures or solutions, that may contain hydrophobic solvents, are extracted continuously or batchwise with 1 to 15 parts of water.

If no hydrophobic solvent is added or only a small amount of hydrophobic solvent is added, large amounts of water are needed for the extraction. If 1 to 2 parts of hydrophobic solvent is added, on the other hand, only a small amount of water is needed.

The extraction is generally carried out at low temperatures. The temperature is preferably 10° to 30° C.

The glycosides are in the aqueous phase and are neutralized with a base or basic ion exchanger. Minimal traces of color still present can be eliminated with activated charcoal. However, this post-treatment is not generally necessary.

The glycosides are isolated by known procedures, for example by evaporation. The glycosides are colorless or light yellow and are odorless.

The dyes and other byproducts are found in the organic phase and can be isolated by evaporation.

The process has the following advantages:

(1) The butyloligoglycosides obtained have very good color quality.

(2) The butyloligoglycosides obtained are odorless.

(3) The butyloligoglycosides obtained are very stable in color. Almost no discolorations occur in transacetalization, and the transacetalization products are of high purity.

(4) The process is simple and can be carried out continuously.

Other features of the invention will become apparent in the course of the following descriptions of exemplary embodiments which are given for illustration of the invention and are not intended to be limiting thereof.

EXAMPLES

Examples 1 to 4, Comparison Examples A and B 1000 parts of n-butanol, 100 parts of natural cornstarch, and 1 part of sulfuric acid are heated in an autoclave at 165° C. for 40 minutes. A solution of butyloligoglucoside (degree of oligomerization approximately 1.2) in butanol is obtained as a black product.

For each experiment, 100 g of the solution is placed in a separatory funnel and mixed with 100 g of toluene and the amount of 0.1N sodium hydroxide indicated in Table 1. The mixture is then extracted twice with 100 g of water. The iodine color numbers of the extracts are listed in Table 1.

After neutralization of the aqueous solutions with 0.1N sodium hydroxide solution or 0.1N sulfuric acid, the solvent is evaporated at 60° C. under vacuum, by which butyloligoglucoside is obtained as a syrup.

The organic phases have an iodine color number of 15 to 20 and also contain dark brown colorants.

Obviously, numerous modifications and variations of the present invention are possible in light of the above teachings. It is therefore to be understood that within the scope of the appended claims, the invention may be practiced otherwise than as specifically described herein.

TABLE 1

| Example | 0.1 N NaOH ml | Acid Number mg KOH/g | Iodine Color Number Extract 1 | Iodine Color Number Extract 2 |
| --- | --- | --- | --- | --- |
| 1 | 5.95 | 0.33 | 1 | 1 |
| 2 | 8.925 | 0.17 | 2 | 1 |
| 3 | 10.4 | 0.08 | 4 | 1–2 |
| 4 | 11.9 | 0 | 7–10 | 2 |
| A | 13.38 | Alkaline | 15 | 2 |
| B | 14.87 | Alkaline | 15–20 | 2 |

What is claimed as new and desired to be secured by Letters Patent of the United States is:

1. A process for producing colorless or light colored butylglycosides or butyloligoglycosides from a crude butylglycoside or butyloligoglycoside reaction product containing colored impurities, comprising the steps of:
   adjusting the acid number of said crude reaction product to 0–12 mg KOH/g by adding an acid or base to said reaction product;
   extracting said adjusted reaction produve with water to produce a water extract containing said butylglycosides or butyloligoglycosides and a residual crude produce containing the colored impurities; and
   isolating said butylglycoside or butyloligoglycoside from said water extract.

2. The process of claim 1, further comprising adding up to 2 parts of a hydrophobic solvent per part of crude reaction produce before said adjusting step.

3. The process of claim 1, wherein said crude reaction product is a reaction product of saccharides and n-butanol.

4. The process of claim 1, wherein said acid number is adjusted to 0.01–3 mg KOH/g.

5. The process of claim 4, wherein said acid number is adjusted to 0.05–1 mg KOH/g.

6. The process of claim 2, wherein two parts of said hydrophobic solvent are added per one part of said crude product.

7. The process of claim 2, wherein said hydrophobic solvent is an aromatic hydrocabon.

8. The process of claim 7, wherein said aromatic hydrocarbon is a member selected from the group consisting of toluene, xylene and mixtures thereof.

9. The process of claim 1, further comprising neutralizing said water extract with a base or a basic ion exchanger.

10. The process of claim 9, further comprising treating said neutralized water extract with activated charcoal.

11. The process of claim 1, wherein said extracting step is performed continuously.

12. The process of claim 1 wherein said butylglycosides and butyloligoglycosides are butylglucosides and bulyloligoglucosides.

13. The process of claim 1, wherein said extracting step is conducted with 1–15 parts of water per part of crude reaction product.

* * * * *

UNITED STATES PATENT AND TRADEMARK OFFICE
CERTIFICATE OF CORRECTION

PATENT NO. : 4,820,814

DATED : April 11, 1989

INVENTOR(S) : HARALD LUEDERS

It is certified that error appears in the above-identified patent and that said Letters Patent is hereby corrected as shown below:

Column 4, line 30, change "produve" to --product--.

Column 4, line 47, change "wherein two" to --wherein up to two--.

Signed and Sealed this

Twenty-seventh Day of February, 1990

*Attest:*

JEFFREY M. SAMUELS

*Attesting Officer*     *Acting Commissioner of Patents and Trademarks*